(12) United States Patent
Hammerland, III

(10) Patent No.: US 11,793,520 B2
(45) Date of Patent: Oct. 24, 2023

(54) TRIGGER MECHANISMS FOR SURGICAL INSTRUMENTS AND SURGICAL INSTRUMENTS INCLUDING THE SAME

(71) Applicant: Covidien LP, Mansfield, MA (US)

(72) Inventor: John A. Hammerland, III, Arvada, CO (US)

(73) Assignee: Covidien LP, Mansfield, MA (US)

( * ) Notice: Subject to any disclaimer, the term of this patent is extended or adjusted under 35 U.S.C. 154(b) by 144 days.

(21) Appl. No.: 17/398,474

(22) Filed: Aug. 10, 2021

(65) Prior Publication Data

US 2021/0361287 A1 Nov. 25, 2021

Related U.S. Application Data

(63) Continuation of application No. 16/558,477, filed on Sep. 3, 2019, now Pat. No. 11,090,050.

(51) Int. Cl.
| | |
|---|---|
| *A61B 17/072* | (2006.01) |
| *A61B 34/00* | (2016.01) |
| *A61B 17/00* | (2006.01) |
| *A61B 17/29* | (2006.01) |

(52) U.S. Cl.
CPC ........ *A61B 17/07207* (2013.01); *A61B 34/76* (2016.02); *A61B 2017/00398* (2013.01); *A61B 2017/00734* (2013.01); *A61B 2017/2925* (2013.01); *A61B 2017/2946* (2013.01)

(58) Field of Classification Search
CPC .... A61B 17/07207; A61B 34/76; A61B 18/04
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler et al. |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |

(Continued)

*Primary Examiner* — Nathaniel C Chukwurah
(74) *Attorney, Agent, or Firm* — Carter, DeLuca & Farrell LLP

(57) ABSTRACT

A trigger assembly of a surgical instrument includes a trigger, a first linkage, a second linkage, and a slider block configured such that moving the manipulation portion in a first direction relative to a housing of the surgical instrument translates the slider block along a longitudinal axis relative to the housing. Another trigger assembly of a surgical instrument includes a trigger and a coupling sphere rotatably captured within a cavity of a retention portion of the trigger such that movement of a manipulation portion of the trigger relative to the housing translates the coupling sphere along the longitudinal axis relative to the housing.

20 Claims, 11 Drawing Sheets

(56) References Cited

U.S. PATENT DOCUMENTS

| | | |
|---|---|---|
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Kamiyama et al. |
| 5,176,695 A | 1/1993 | Dulebohn |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,496,317 A | 3/1996 | Goble et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,535 A | 11/1996 | Viklund |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Backer et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,667,526 A | 9/1997 | Levin |
| 5,674,220 A | 10/1997 | Fox et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,779,701 A | 7/1998 | McBrayer et al. |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,958 A | 8/1998 | Yoon |
| 5,800,449 A | 9/1998 | Wales |
| 5,810,808 A | 9/1998 | Eggers |
| 5,810,811 A | 9/1998 | Yates et al. |

(56) References Cited

U.S. PATENT DOCUMENTS

| | | |
|---|---|---|
| 5,814,043 A | 9/1998 | Shapeton |
| 5,817,083 A | 10/1998 | Shemesh et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,876,401 A | 3/1999 | Schulze et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,902,301 A | 5/1999 | Olig |
| 5,906,630 A | 5/1999 | Anderhub et al. |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,976,132 A | 11/1999 | Morris |
| 5,989,277 A | 11/1999 | LeMaire, III et al. |
| 6,004,335 A | 12/1999 | Vaitekunas et al. |
| 6,010,516 A | 1/2000 | Hulka |
| 6,024,741 A | 2/2000 | Williamson, IV et al. |
| 6,024,744 A | 2/2000 | Kese et al. |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,126,658 A | 10/2000 | Baker |
| 6,152,923 A | 11/2000 | Ryan |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,877 B1 | 3/2001 | Kese et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,322,561 B1 | 11/2001 | Eggers et al. |
| 6,334,860 B1 | 1/2002 | Dorn |
| 6,334,861 B1 | 1/2002 | Chandler et al. |
| 6,350,264 B1 | 2/2002 | Hooven |
| 6,352,536 B1 | 3/2002 | Buysse et al. |
| D457,958 S | 5/2002 | Dycus et al. |
| D457,959 S | 5/2002 | Tetzlaff et al. |
| 6,398,779 B1 | 6/2002 | Buysse et al. |
| 6,409,728 B1 | 6/2002 | Ehr et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,970 B1 | 9/2002 | Schulze et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,702 B2 | 10/2002 | Schulze et al. |
| 6,464,704 B2 | 10/2002 | Schmaltz et al. |
| 6,511,480 B1 | 1/2003 | Tetzlaff et al. |
| 6,585,735 B1 | 7/2003 | Frazier et al. |
| 6,620,161 B2 | 9/2003 | Schulze et al. |
| 6,626,901 B1 | 9/2003 | Treat et al. |
| 6,682,528 B2 | 1/2004 | Frazier et al. |
| 6,695,840 B2 | 2/2004 | Schulze |
| 6,726,686 B2 | 4/2004 | Buysse et al. |
| 6,743,229 B2 | 6/2004 | Buysse et al. |
| 6,770,072 B1 | 8/2004 | Truckai et al. |
| D496,997 S | 10/2004 | Dycus et al. |
| D499,181 S | 11/2004 | Dycus et al. |
| 7,150,749 B2 | 12/2006 | Dycus et al. |
| 9,655,673 B2 | 5/2017 | McCullough, Jr. et al. |
| 11,090,050 B2 | 8/2021 | Hammerland, III |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0109875 A1 | 6/2003 | Tetzlaff et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0229344 A1 | 12/2003 | Dycus et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0225288 A1 | 11/2004 | Buysse et al. |
| 2004/0236325 A1 | 11/2004 | Tetzlaff et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1* | 12/2004 | Dycus ............. A61B 18/1482 606/51 |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2016/0074097 A1* | 3/2016 | Nutting ............. A61B 18/1445 606/51 |

\* cited by examiner

TRIGGER MECHANISMS FOR SURGICAL INSTRUMENTS AND SURGICAL INSTRUMENTS INCLUDING THE SAME

CROSS-REFERENCE TO RELATED APPLICATIONS

This application is a continuation of U.S. patent application Ser. No. 16/558,477, filed on Sep. 3, 2019, the entire contents of which are hereby incorporated herein by reference.

FIELD

The present disclosure relates to surgical instruments and, more particularly, to trigger mechanisms for surgical instruments and surgical instruments including the same.

BACKGROUND

A surgical forceps is a pliers-like surgical instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife or cutting member utilized to effectively sever the treated tissue.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a trigger assembly of a surgical instrument that includes a trigger, a first linkage, a second linkage, e.g., a T-linkage, and a slider block. The trigger includes a manipulation portion, a linkage portion, and a pivot portion disposed between the manipulation and linkage portions. The pivot portion is configured for pivotable engagement with a housing of a surgical instrument such that moving the manipulation portion in a first direction relative to the housing pivots the pivot portion relative to the housing to thereby move the linkage portion in a second, opposite direction relative to the housing. The first linkage defines a first floating end portion and a second pivoting end portion. The second pivoting end portion is configured for pivotable engagement with the housing. The second linkage includes a crossbar and an upright. The crossbar is pivotably coupled to and extends between the linkage portion of the trigger and the first floating end portion of the first linkage. The slider block is operably engaged with the upright of the second linkage such that movement of the upright in response to movement of the manipulation portion of the trigger relative to the housing translates the slider block along a longitudinal axis relative to the housing.

In an aspect of the present disclosure, the manipulation portion of the trigger is disposed on one side of the longitudinal axis and the linkage portion of the trigger is pivotably coupled to the crossbar of the second linkage on a second, opposite side of the longitudinal axis. Additionally or alternatively, the linkage portion of the trigger traverses the longitudinal axis.

In another aspect of the present disclosure, the second pivoting end portion of the first linkage is disposed on one side of the longitudinal axis and the first floating end portion of the trigger is pivotably coupled to the crossbar of the second linkage on a second, opposite side of the longitudinal axis. Additionally or alternatively, the first linkage includes a body extending between the first floating end portion and the second pivoting end portion and traversing the longitudinal axis.

In another aspect of the present disclosure, the slider block is operably engaged with the upright of the second linkage via a post-opening, e.g., post-slot, post-aperture, etc. engagement such that, in response to longitudinal and vertical motion of the upright of the second linkage, the slider block is only moved longitudinally.

In still another aspect of the present disclosure, the first linkage is arcuate and defines a distally-facing concave side and a proximally-facing convex side. In such aspects, the concave side of the first linkage may define a volume wherein the slider block is disposed in the volume in at least one position of the manipulation portion of the trigger relative to the housing.

In yet another aspect of the present disclosure, at least a portion of at least one of: the trigger, the second linkage, or the first linkage defines a bifurcated configuration for receipt of a drive bar therebetween.

In still yet another aspect of the present disclosure, at least one of: the trigger, the second linkage, or the first linkage is formed as a single, monolithic piece of material.

Another trigger assembly of a surgical instrument provided in accordance with the present disclosure includes a trigger and a coupling sphere. The trigger includes a manipulation portion, a retention portion, and a pivot portion disposed between the manipulation and retention portions. The pivot portion is configured for pivotable engagement with a housing of a surgical instrument such that moving the manipulation portion in a first direction relative to the housing pivots the pivot portion relative to the housing to thereby move the retention portion in a second, opposite direction relative to the housing. The retention portion defines a cavity. The coupling sphere is rotatably captured within the cavity of the retention portion. At least a portion of the cavity defines an internal surface complementary to an external surface of the coupling sphere such that movement of the manipulation portion of the trigger relative to the housing translates the coupling sphere along a longitudinal axis relative to the housing.

In an aspect of the present disclosure, the manipulation portion of the trigger is disposed on one side of the longitudinal axis and the retention portion of the trigger extends to a second, opposite side of the longitudinal axis.

In another aspect of the present disclosure, the trigger is formed as a single, monolithic piece of material.

In still another aspect of the present disclosure, the coupling sphere is formed from first and second components engaged with one another via snap-fitting.

In yet another aspect of the present disclosure, the coupling sphere is configured for positioning about a drive bar.

In still yet another aspect of the present disclosure, the coupling sphere includes an internal post extending therethrough.

In another aspect of the present disclosure, the retention portion of the trigger includes first and second spaced-apart side walls configured for positioning on opposing sides of the coupling sphere. In such aspects, the first and second spaced-apart side walls may include proximal and distal ends extending inwardly to retain the coupling sphere longitudinally therebetween.

In another aspect of the present disclosure, the retention portion of the trigger includes proximal and distal fork ends configured for positioning at proximal and distal ends, respectively, of the coupling sphere. In such aspects, the distal fork end may include a connector connecting first and second fork legs thereof.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
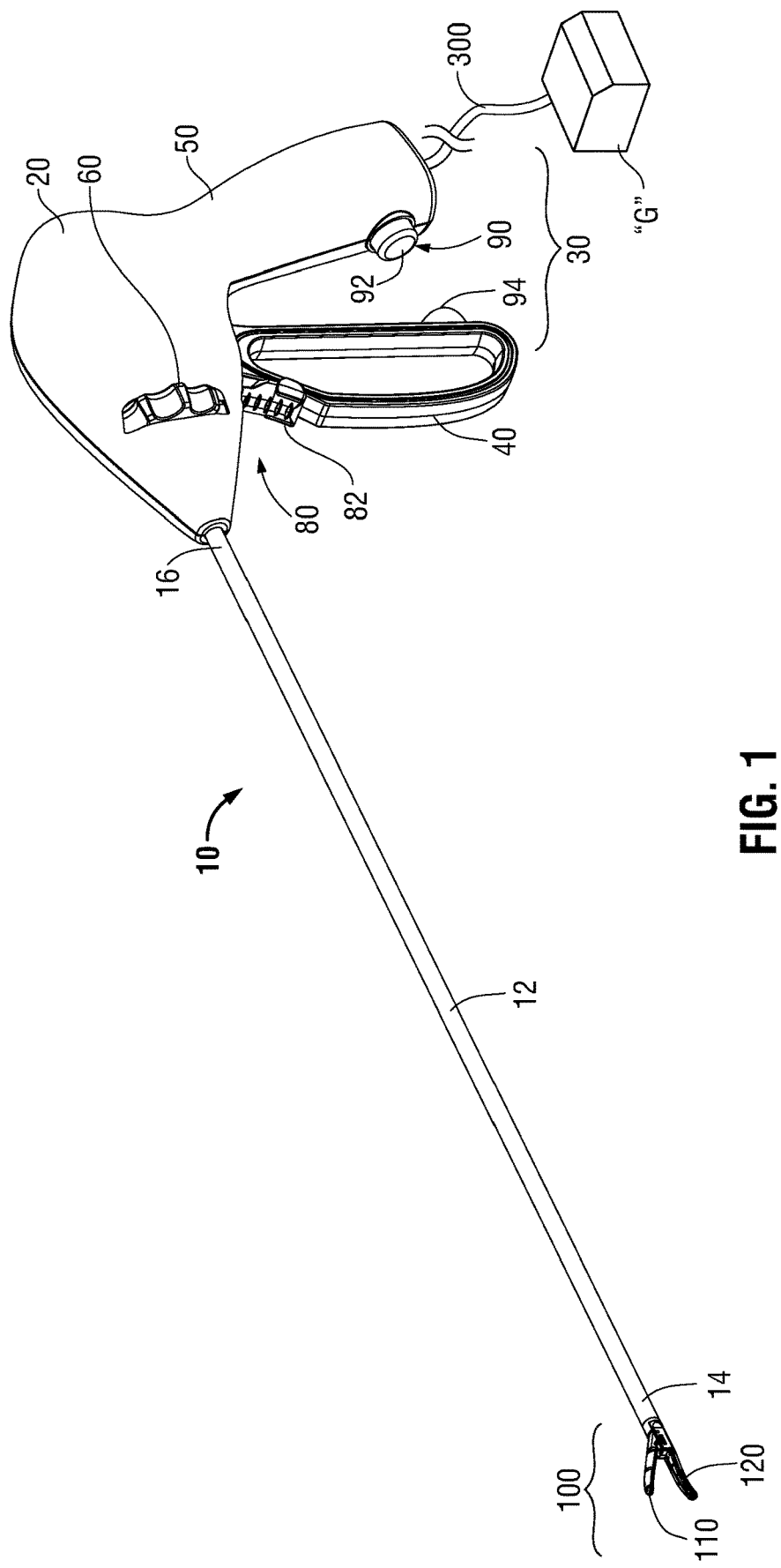
FIG. 1 is a perspective view of an electrosurgical forceps provided in accordance with the present disclosure.

Referring to FIG. 1, a surgical instrument provided in accordance with the present disclosure is shown configured as a bipolar electrosurgical forceps 10 for use in connection with endoscopic surgical procedures, although the present disclosure is equally applicable for use with other surgical instruments such as those for use in endoscopic and/or traditional open surgical procedures. Forceps 10 generally includes a housing 20, a handle assembly 30, a rotating assembly 60, a trigger assembly 80, an activation assembly 90, and an end effector assembly 100 including first and second jaw members 110, 120.

Forceps 10 further includes a shaft 12 having a distal end portion 14 configured to engage (directly or indirectly) end effector assembly 100 and a proximal end portion 16 that engages (directly or indirectly) housing 20. Rotating assembly 60 is rotatable in either direction to rotate shaft 12 and end effector assembly 100 relative to housing 20 in either direction. Housing 20 houses the internal working components of forceps 10.

An electrosurgical cable 300 connects forceps 10 to an electrosurgical generator "G" or other suitable energy source, although forceps 10 may alternatively be configured as a handheld instrument incorporating energy-generating and/or power components thereon or therein. Cable 300 includes wires (not shown) extending therethrough, into housing 20, and through shaft 12, to ultimately connect electrosurgical generator "G" to jaw member 110 and/or jaw member 120 of end effector assembly 100. Activation button 92 of activation assembly 90 is disposed on housing 20 are electrically coupled between end effector assembly 100 and cable 300 to enable the selective supply of energy to jaw member 110 and/or jaw member 120, e.g., upon activation of activation button 92. However, other suitable electrical connections and/or configurations for supplying electrosurgical energy to jaw member 110 and/or jaw member 120 may alternatively be provided, as may other suitable forms of energy, e.g., ultrasonic energy, microwave energy, light energy, thermal energy, etc.

Forceps 10 additionally includes a knife assembly 170 (FIG. 2A) operably coupled to trigger assembly 80 and extending through housing 20 and shaft 12. One or both of jaw members 110, 120 defines a knife channel 125 (FIG. 2A) configured to permit reciprocation of a knife blade 172 (FIG. 2A) of knife assembly 170 (FIG. 2A) therethrough, e.g., in response to actuation of trigger 82 of trigger assembly 80. Trigger assembly 80 is described in greater detail below as are other embodiments of trigger assemblies configured for use with forceps 10.

Figure 2A:
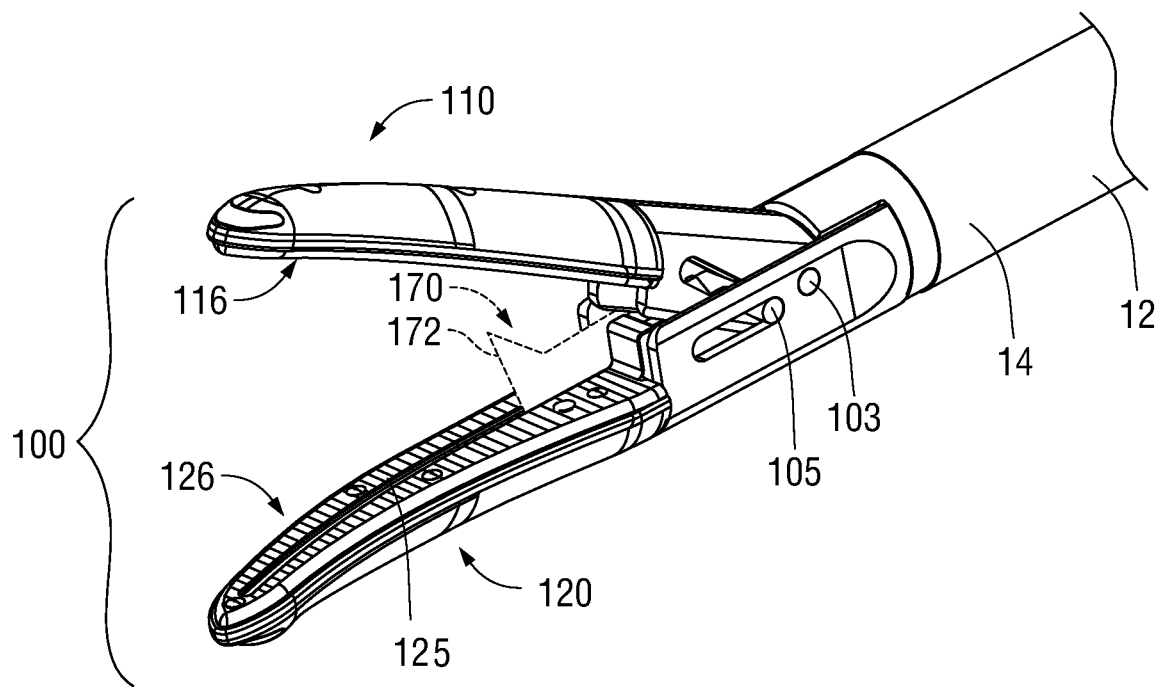
FIG. 2A is an enlarged, perspective view of an end effector assembly of the electrosurgical forceps of FIG. 1 wherein first and second jaw members of the end effector assembly are disposed in a spaced-apart position.
Figure 2B:
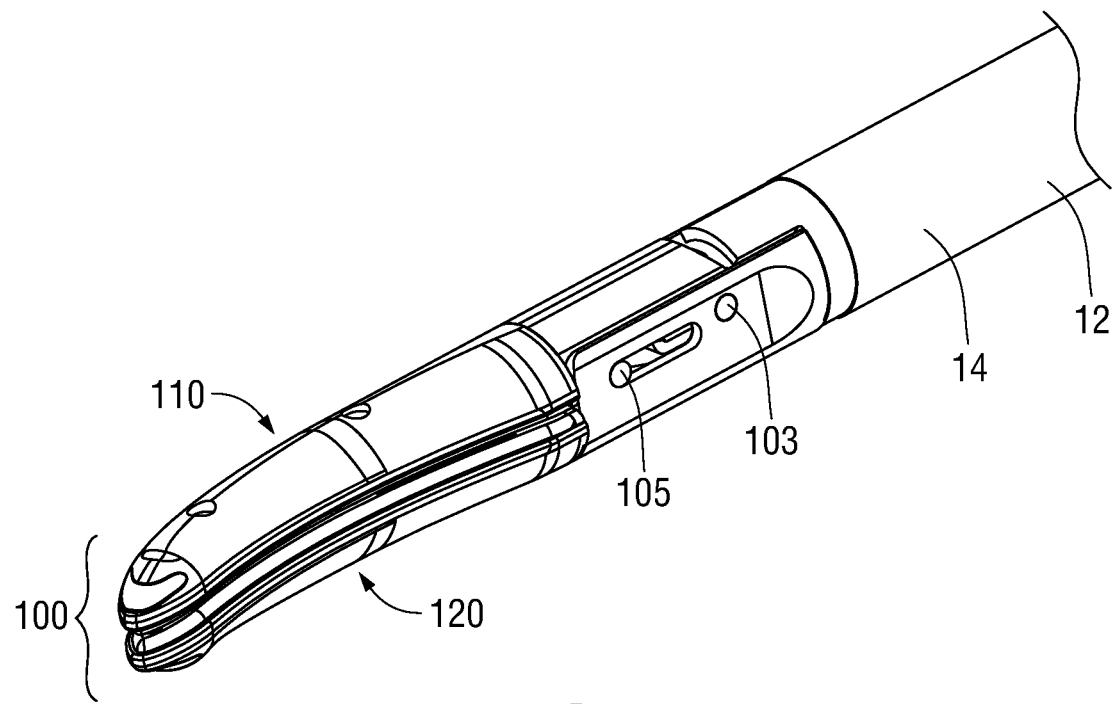
FIG. 2B is an enlarged, perspective view of the end effector assembly of FIG. 2A wherein the first and second jaw members are disposed in an approximated position.
Figure 3A:
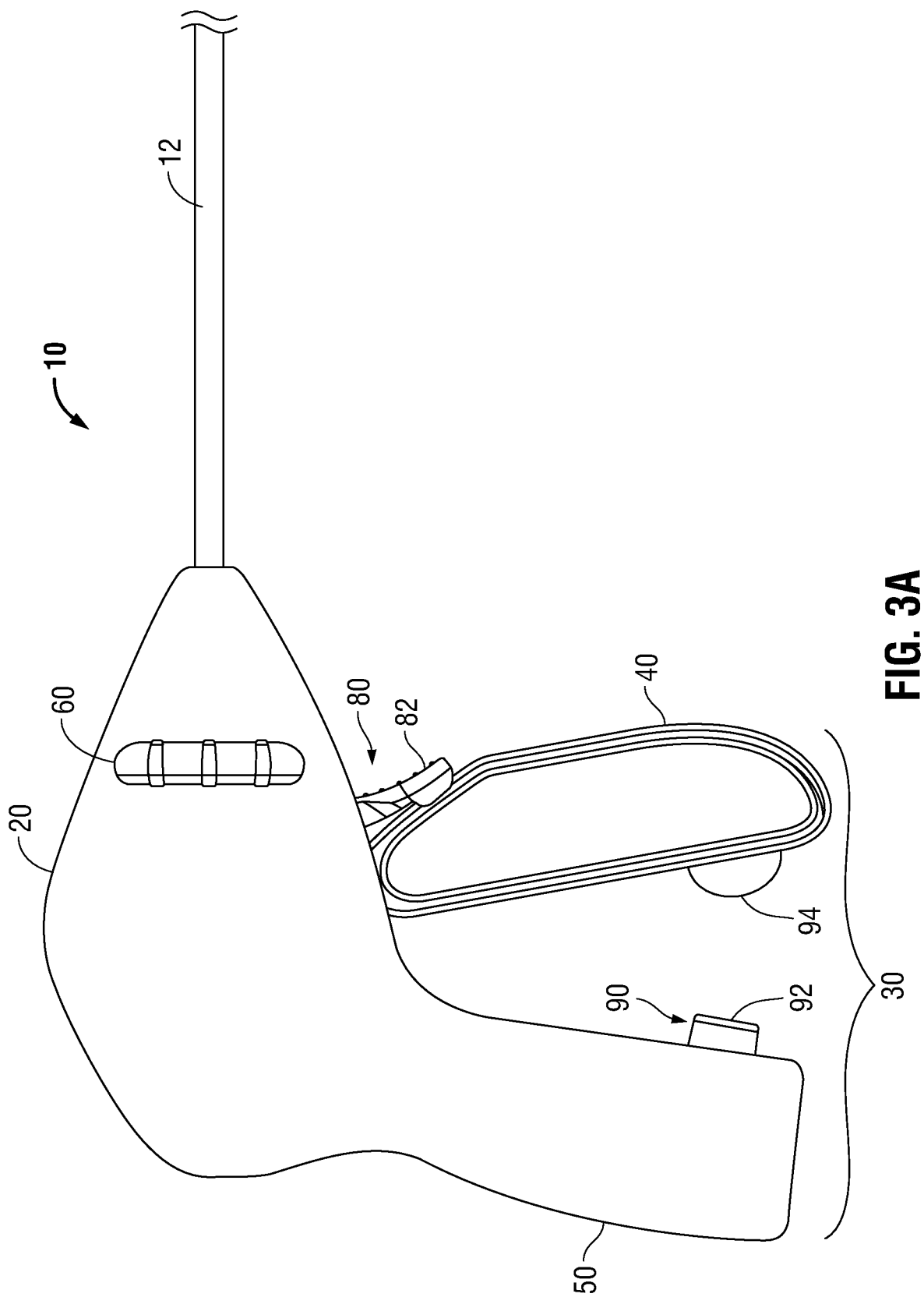
FIG. 3A is a side view of a proximal portion of the electrosurgical forceps of FIG. 1 with a movable handle and trigger thereof disposed in respective un-actuated positions.
Figure 3B:
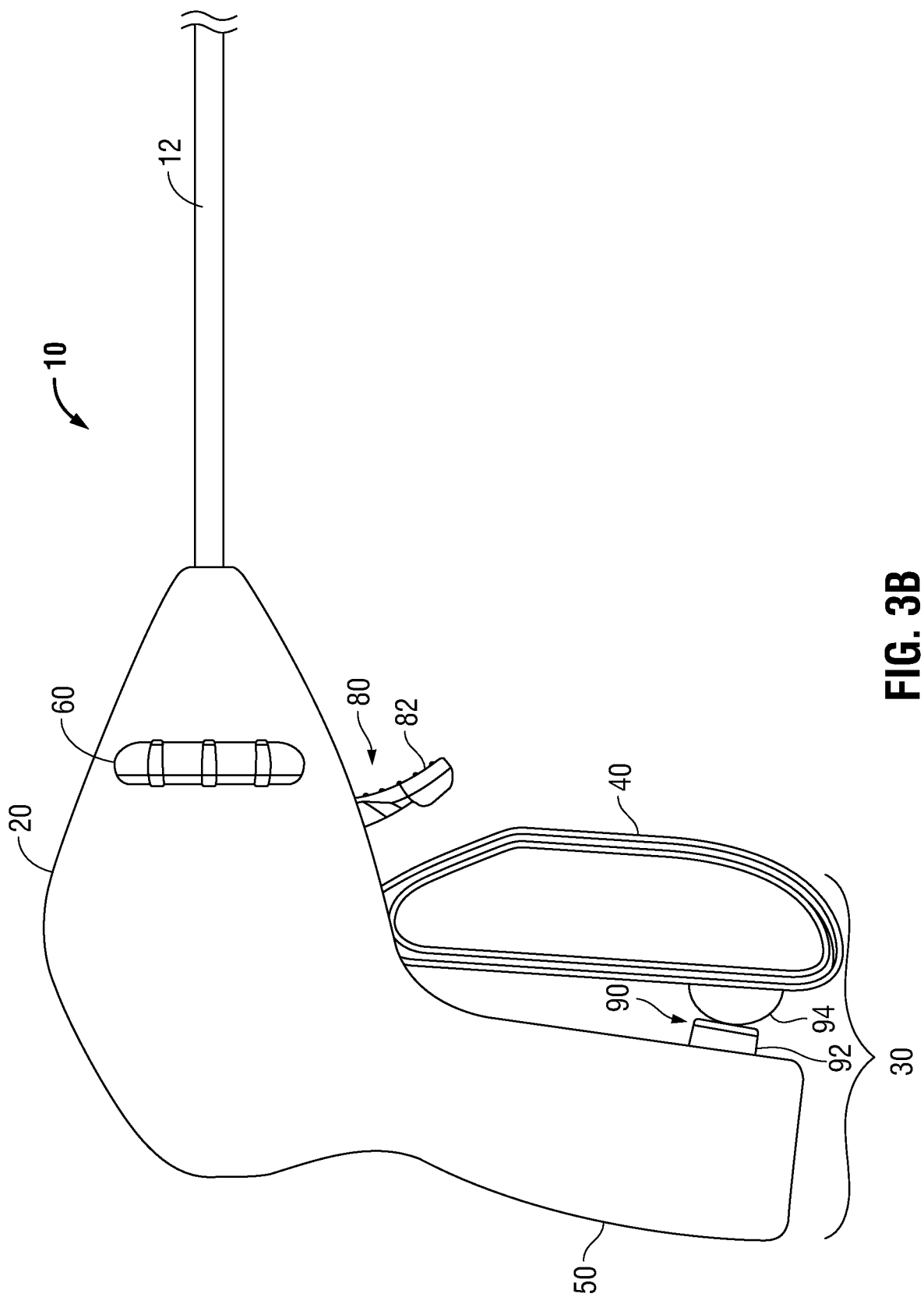
FIG. 3B is a side view of the proximal portion of the electrosurgical forceps shown in FIG. 3A with the movable handle disposed in an actuated position and the trigger disposed in the un-actuated position.
Figure 3C:
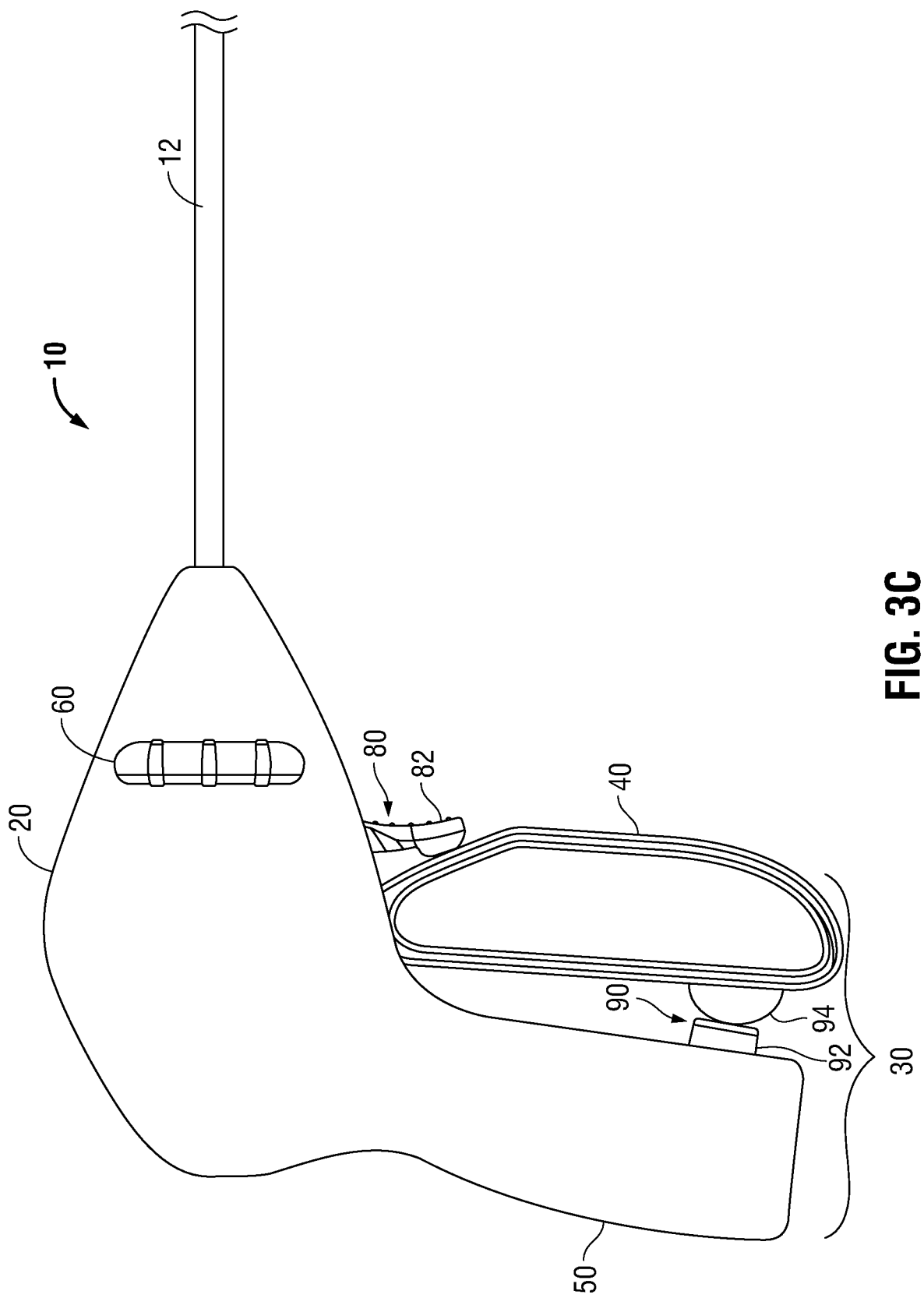
FIG. 3C is a side view of the proximal portion of the electrosurgical forceps shown in FIG. 3A with the movable handle and trigger disposed in respective actuated positions.

With additional reference to FIGS. 2A and 2B, end effector assembly 100, as noted above, is disposed at distal end portion 14 of shaft 12 and includes a pair of jaw members 110 and 120 pivotable between a spaced-apart position and an approximated position for grasping tissue therebetween. End effector assembly 100 is designed as a unilateral assembly, e.g., wherein one of the jaw members 120 is fixed relative to shaft 12 and the other jaw member 110 is movable relative to both shaft 12 and the fixed jaw member 120. However, end effector assembly 100 may alternatively be configured as a bilateral assembly, e.g., wherein both jaw member 110 and jaw member 120 are movable relative to one another and with respect to shaft 12.

Each jaw member 110, 120 of end effector assembly 100 includes an electrically-conductive tissue-contacting surface 116, 126. Tissue-contacting surfaces 116 are positioned to oppose one another for grasping and treating tissue. More specifically, tissue-contacting surfaces 116, 126 are electrically coupled to the generator "G," e.g., via cable 300, and activation button 92 to enable the selective supply of energy thereto for conduction through tissue grasped therebetween, e.g., upon activation of activation button 92. One or both of tissue-contacting surfaces 116, 126 may include one or more stop members (not shown) extending therefrom to define a minimum gap distance between electrically-conductive tissue-contacting surfaces 116, 126 in the approximated position of jaw members 110, 120, facilitate grasping of tissue, and/or inhibit shorting between electrically-conductive tissue-contacting surfaces 116, 126. The stop member(s) may be formed at least partially from an electrically-insulative material or may be effectively insulative by electrically isolating the stop member(s) from one or both of the electrically-conductive tissue-contacting surfaces 116, 126.

A pivot pin 103 of end effector assembly 100 extends transversely through aligned apertures defined within jaw members 110, 120 and shaft 12 to pivotably couple jaw member 110 to jaw member 120 and shaft 12. A cam pin 105 of end effector assembly 100 extends transversely through cam slots defined within jaw members 110, 120 and is operably engaged with a distal end portion of a drive bar 152 (FIGS. 4A and 4B) of a drive assembly (only drive bar 152 (FIGS. 4A and 4B) of the drive assembly is shown) such that longitudinal translation of drive bar 152 (FIGS. 4A and 4B) through shaft 12 translates cam pin 105 relative to jaw members 110, 120. More specifically, distal translation of cam pin 105 relative to jaw members 110, 120 urges cam pin 105 distally through the cam slots to thereby pivot jaw members 110, 120 from the spaced-apart position towards the approximated position, although cam slots may alternatively be configured such that proximal translation of cam pin 105 pivots jaw members 110, 120 from the spaced-apart position towards the approximated position. One suitable drive assembly is described in greater detail, for example, in U.S. Pat. No. 9,655,673, the entire contents of which are hereby incorporated herein by reference.

Referring to FIGS. 1-3C, handle assembly 30 includes a fixed handle 50 and an actuator, e.g., movable handle 40. Fixed handle 50 is integrally associated with housing 20 and movable handle 40 is movable relative to fixed handle 50. Movable handle 40 is ultimately connected to the drive assembly (not shown) that, together, mechanically cooperate to impart movement of jaw members 110 and 120 between the spaced-apart and approximated positions to grasp tissue between electrically-conductive surfaces 116, 126, respectively. More specifically, pivoting of movable handle 40 relative to fixed handle 50 from an un-actuated position towards an actuated position pivots jaw members 110, 120 from the spaced-apart position towards the approximated position. On the other hand, when movable handle 40 is released or returned towards the initial position relative to fixed handle 50, jaw members 110, 120 are returned towards the spaced-apart position. A biasing spring (not shown) associated with movable handle 40 and/or the drive assembly may be provided to bias jaw members 110, 120 towards a desired position, e.g., the spaced-apart position or the approximated position.

Fixed handle 50 operably supports activation button 92 of activation assembly 90 thereon in an in-line position, wherein activation button 92 is disposed in the actuation path of movable handle 40. In this manner, upon pivoting of movable handle 40 relative to fixed handle 50 from the actuated position to an activated position, protrusion 94 of movable handle 40 is urged into contact with activation button 92 to thereby activate activation button 92 and initiate the supply of energy to electrically-conductive surfaces 116, 126, e.g., to treat tissue grasped therebetween. Alternatively, actuation button 92 may be disposed in any other suitable position, on housing 20 or remote therefrom, to facilitate manual activation by a user to initiate the supply of energy to electrically-conductive surfaces 116, 126.

With reference to FIGS. 1-2B and 4A-4B, as noted above, trigger assembly 80 is operably coupled to knife blade 172 of knife assembly 170. More specifically, trigger 82 of trigger assembly 80 is selectively actuatable, e.g., from an un-actuated position (FIGS. 3A and 4A) to an actuated position (FIGS. 3C and 4B), to deploy knife blade 172 distally through jaw members 110, 120 to cut tissue grasped between electrically-conductive surfaces 116, 126. Knife assembly 170 includes knife blade 172 and a knife bar 174 engaged with and extending proximally from knife blade 172 through shaft 12 and drive bar 152 into housing 20 where knife bar 174 is operably coupled with trigger assembly 80, as detailed below.

Figure 4A:
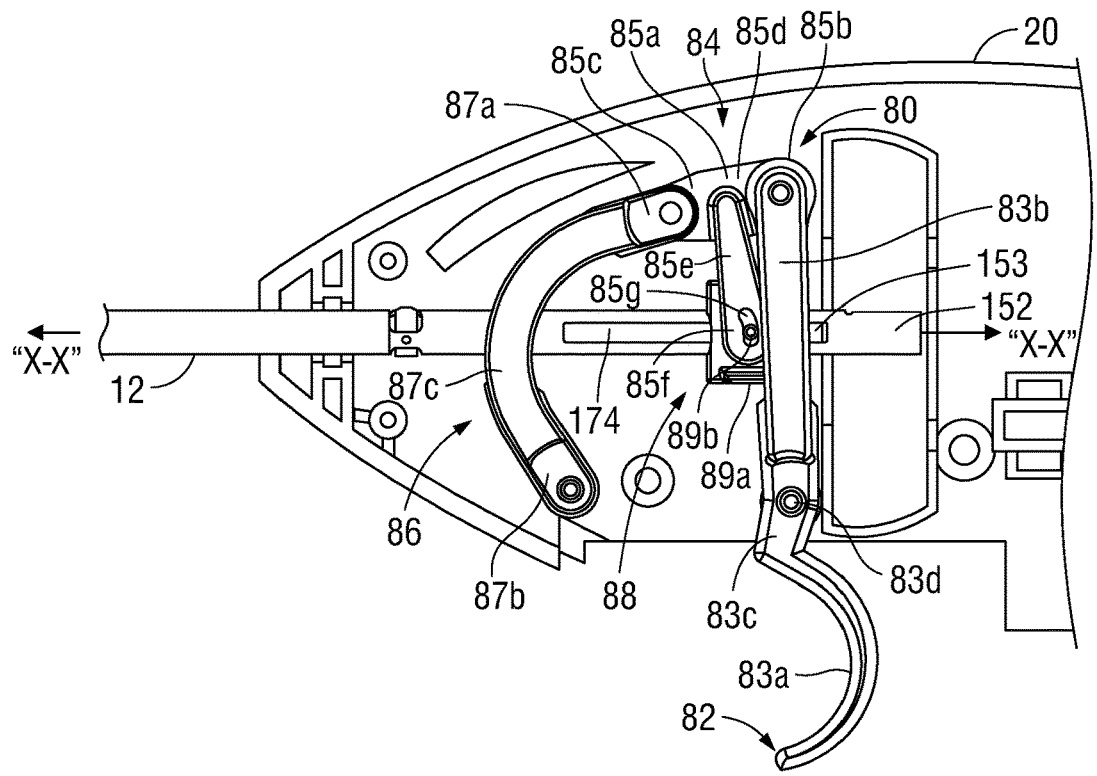
FIG. 4A is a side view of another proximal portion of the electrosurgical forceps of FIG. 1 with portions removed to illustrate a trigger assembly thereof with the trigger disposed in the un-actuated position.
Figure 4B:
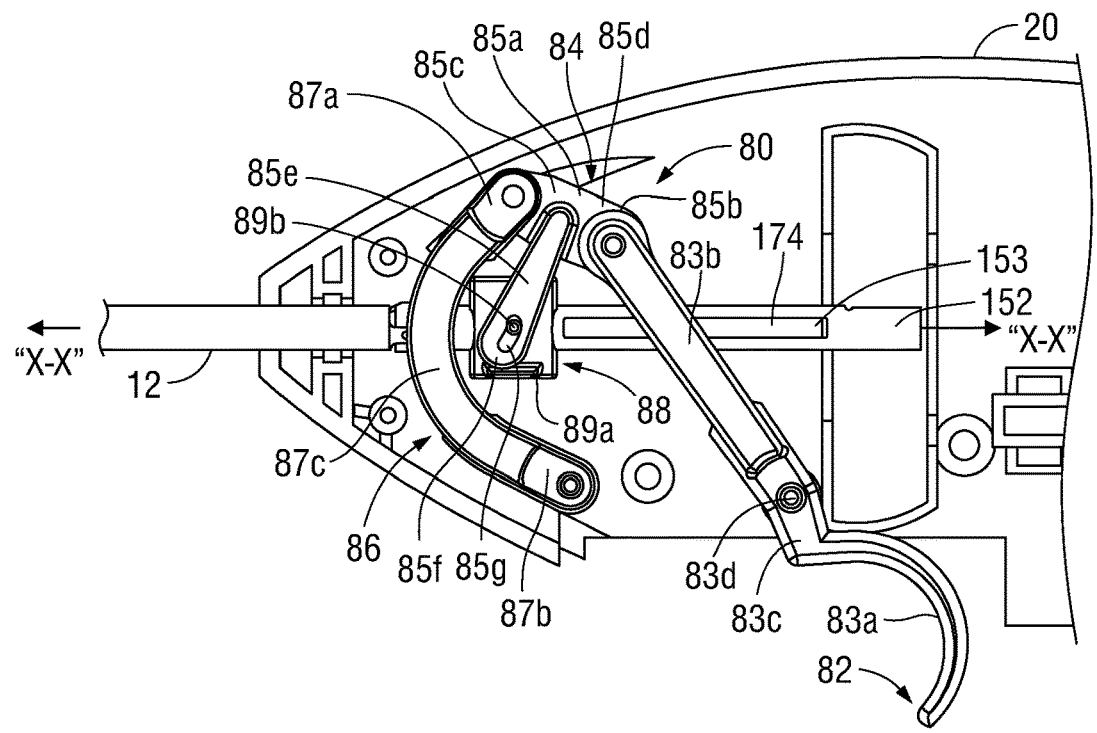
FIG. 4B is a side view of the proximal portion of the electrosurgical forceps shown in FIG. 4A with portions removed to illustrate the trigger assembly with the trigger disposed in the actuated position.

Referring to FIGS. 4A and 4B, trigger assembly 80 includes trigger 82, a link 84, e.g., a T-link 84, a link 86, e.g., an arcuate linkage 86 although other configurations, e.g., linear, angled, etc. are also contemplated, and a slider block 88. In this manner, trigger assembly 80 defines a four-bar mechanical linkage assembly for driving slider block 88. An upright 85e of T-link 84, a body 87c of arcuate link 86, and a linkage portion 83b of trigger 82 define bifurcated configurations including first and second spaced-apart segments disposed on either side of drive bar 152. The first and second segments are mirror-images of one another and, thus, upright 85e of T-link 84, body 87c of arcuate link 86, and linkage portion 83b of trigger 82 are detailed below in the singular for simplicity purposes. As an alternative to bifurcated configurations, one or more of upright 85e of T-link 84, body 87c of arcuate link 86, and linkage portion 83b of trigger 82 may include only one segment, e.g., disposed on one side of drive bar 152.

Trigger 82 includes a manipulation portion 83a extending from housing 20 to enable manual manipulation thereof by a user. Trigger 82 further includes a linkage portion 83b and a pivot portion 83c. Trigger 82 is monolithically formed from a single piece of material or is otherwise formed, e.g., via fixed engagements, such that manipulation portion 83a, linkage portion 83b, and pivot portion 83c are fixed relative to one another. Pivot portion 83c is pivotably coupled within housing 20 via receipt of a pair of pivot posts 83d extending outwardly from opposite sides of pivot portion 83c within corresponding apertures (not shown) defined on opposed interior sides of housing 20. Pivot portion 83c is pivotably coupled to housing 20 at a position below a longitudinal axis "X-X" defined by shaft 12, drive bar 152, and/or knife bar 172. Further, pivot portion 83c is disposed between manipulation portion 83a, which extends from housing 20, and linkage portion 83b, which is disposed within housing 20, such that movement of manipulation portion 83a in one direction, e.g., proximally, urges linkage portion 83b in the opposite direction, e.g., distally. However, other configurations are also contemplated, e.g., wherein pivot portion 83c is offset relative to manipulation portion 83a and/or linkage portion 83b.

Linkage portion 83b of trigger 82 extends from pivot portion 83c below longitudinal axis "X-X" to a free end portion thereof above longitudinal axis "X-X" and is pivotably coupled at the free end portion thereof to a proximal end portion 85b of a crossbar 85a of T-link 84. T-link 84 includes crossbar 85a defining proximal and distal end portions 85b, 85c, respectively, and an upright 85e extending from an intermediate portion 85d of crossbar 85a between proximal and distal end portions 85b, 85c, respectively, e.g., in generally perpendicular orientation or other suitable orientation relative to crossbar 85a. Upright 85e of T-link 84 is fixed relative to, e.g., monolithically formed with intermediate portion 85d of crossbar 85a at a position above longitudinal axis "X-X" and extends downwardly therefrom to a free end portion 85f defining a slot 85g. Slot 85g extends to or traverses longitudinal axis "X-X" and is configured to receive an outwardly-extending pivot post 89b extending outwardly from body 89a of slider block 88.

Arcuate link 86 includes an upper end portion 87a, a lower end portion 87b, and a body 87c extending between upper and lower end portions 87a, 87b, respectively. Upper end portion 87a of arcuate link 86 is disposed above longitudinal axis "X-X" and is pivotably coupled to distal end portion 85c of crossbar 85a of T-link 84 above longitudinal axis "X-X." Body 87c of arcuate link 86 traverses longitudinal axis "X-X" from extending from upper end portion 87a of arcuate link 86 is to lower end portion 87b of arcuate link 86. Lower end portion 87b of arcuate link 86 is disposed below longitudinal axis "X-X" and is pivotably coupled to housing 20, e.g., via a pivot pin, below longitudinal axis "X-X". Body 87c of arcuate link 86, in embodiments, defines an arcuate configuration wherein the concave side thereof is proximally-facing and the convex side thereof is distally-facing. This configuration provides suitable clearance to enable receipt of slider block 88 within the concave volume defined by body 87c on the concave side thereof. Alternatively, as noted above, link 86 need not be arcuate but may define a linear, angled, or other suitable configuration.

Slider block 88, as noted above, includes a body 89a and an outwardly-extending pivot post 89b extending outwardly from body 89a. Body 89a of slider block 88 is slidably disposed about drive bar 152 and includes an internal post, posts, or other suitable engagement structure(s) (not shown) extending through a longitudinal slot 153 defined within drive bar 152 and into engagement with knife bar 174 to fix body 89a of slider block 88 relative to knife bar 174. Slider block 88 is slidable about drive bar 152 and along longitudinal axis "X-X" to thereby translate knife bar 174 to, in turn, deploy knife blade 172 distally through jaw members 110, 120 to cut tissue grasped between electrically-conductive surfaces 116, 126 and to retract knife blade 172 subsequent to tissue cutting (see FIG. 2A).

Continuing with reference to FIGS. 4A and 4B, as a result of the above-detailed configuration, moving manipulation portion 83a of trigger 82 proximally relative to housing 20, e.g., from the un-actuated position (FIG. 4A) towards the actuated position (FIG. 4B), rotates pivot portion 83c counterclockwise (from the orientation illustrated in FIGS. 4A and 4B) relative to housing 20 to thereby move linkage portion 83b distally. This distal movement of linkage portion 83b urges T-link 84 distally. More specifically, the distal movement of linkage portion 83b urges crossbar 85a distally to thereby urge upper end portion 87a of arcuate linkage 86 distally such that lower end portion 87b of arcuate linkage 86 is rotated counterclockwise (from the orientation illustrated in FIGS. 4A and 4B) relative to housing 20 about the pivot coupling lower end portion 87b with housing 20. Further, the distal movement of linkage portion 83b urges crossbar 85a distally to thereby pull upright 85e distally along with crossbar 85a. As upright 85e is pulled distally, pivot post 89b, which is received within slot 85g of upright 85e, is likewise pulled distally such that body 89a of slider block 88 is pulled distally about drive bar 152 and relative to housing 20 and shaft 12. This distal translation of slider block 88 translates knife bar 174 distally through shaft 12 and relative to end effector assembly 100 to deploy knife blade 172 distally through jaw members 110, 120 to cut tissue grasped between electrically-conductive surfaces 116, 126 (see FIG. 2A).

It is noted that slot 85g enables upright 85e to include a relatively minor vertical range of motion in response to pivoting of trigger 82 and arcuate linkage 86, without imparting vertical motion to slider block 88. In embodiments, slot 85g may be cam-shaped to vary the mechanical advantage during travel. Further, the above-detailed configuration provides a four-bar mechanical linkage facilitating deployment of knife blade 172 (FIG. 2A) in response to pivoting of trigger 82. In embodiments, a return spring (not shown) may be provided to return manipulation portion 83a of trigger 82 towards the un-actuated position and, thus, to return knife blade 172 to the retracted position (FIG. 2A). Upon release of manipulation portion 83a of trigger 82 (in embodiments where a return spring is provided) or return of manipulation portion 83a of trigger 82 towards the un-actuated position, trigger 82 is pivoted clockwise (from the orientation illustrated in FIGS. 4A and 4B) relative to housing 20 to rotate pivot portion 83c clockwise (from the orientation illustrated in FIGS. 4A and 4B) relative to housing 20 to thereby move linkage portion 83b proximally. This proximal movement of linkage portion 83b pulls T-link 84 proximally, pulling crossbar 85a proximally to thereby pull upper end portion 87a of arcuate linkage 86 proximally such that lower end portion 87b of arcuate linkage 86 is rotated clockwise (from the orientation illustrated in FIGS. 4A and 4B) relative to housing 20 about the pivot coupling lower end portion 87b with housing 20. As a result of the above, upright 85e is moved proximally such that pivot post 89b, which is received within slot 85g of upright 85e, is likewise moved proximally to translate slider block 88 proximally about drive bar 152 and relative to housing 20 and shaft 12, thereby retracting knife blade 172 proximally from jaw members 110, 120 (see FIG. 2A).

Turning to FIGS. 5A-7C, another embodiment of a trigger mechanism 180 configured for use with forceps 10 (FIG. 1) is shown. Trigger mechanism 180 includes a trigger 182 and a coupling sphere 188.

Referring in particular to FIGS. 5A-5C and 7A-7C, trigger 182 includes a manipulation portion 183a extending from housing 20 to enable manual manipulation thereof by a user. Trigger 182 further includes a retention portion 183b and a pivot portion 183c. Trigger 182 is monolithically formed from a single piece of material or is otherwise formed, e.g., via fixed engagements, such that manipulation portion 183a, retention portion 183b, and pivot portion 183c are fixed relative to one another. Pivot portion 183c is pivotably coupled within housing 20 via receipt of a pair of pivot posts 183d extending outwardly from opposite sides of pivot portion 183c within corresponding apertures (not shown) defined on opposed interior sides of housing 20. Alternatively, this configuration may be reversed, e.g., wherein apertures are defined within pivot portion 183c and posts extend inwardly from housing 20, or a pivot pin can be used to couple pivot portion 183c and housing 20 with one another. Pivot portion 183c is pivotably coupled to housing 20 at a position below a longitudinal axis "X-X" defined by shaft 12, drive bar 152, and/or knife bar 172. Further, pivot portion 183c may be disposed between manipulation portion 183a, which extends from housing 20, and retention portion 183b, which is disposed within housing 20, such that movement of manipulation portion 183a in one direction, e.g., proximally, urges retention portion 183b in the opposite direction, e.g., distally. Other configurations are also contemplated.

Retention portion 183b of trigger 182 extends from pivot portion 183c below longitudinal axis "X-X" to meet or traverse longitudinal axis "X-X," although other configurations are also contemplated. Retention portion 183b defines a base 184a and a pair of spaced-apart side walls 184b extending from base 184 on either side of drive bar 152. Base 184a and side walls 184b cooperate to partially enclose a cavity 185 that is aligned on longitudinal axis "X-X." Side walls 184b may define proximal and distal ends 186 (FIG. 7C) that extend radially inwardly, e.g., defining a curvature, so as to partially bound cavity 185 at the proximal and distal ends thereof. Further, cavity 185 is at least partially defined by arcuate interior surfaces of base 184a and/or side walls 184b such that cavity 185 is at least partially complementary to coupling sphere 188, which is rotatably captured within cavity 185 (see FIG. 5C), about a proximal portion of coupling sphere 188 to thereby provided smooth and consistent urging against coupling sphere 188 to translate coupling sphere 188 distally as retention portion 183b is moved distally and rotated about pivot portion 183c.

Figure 5A:
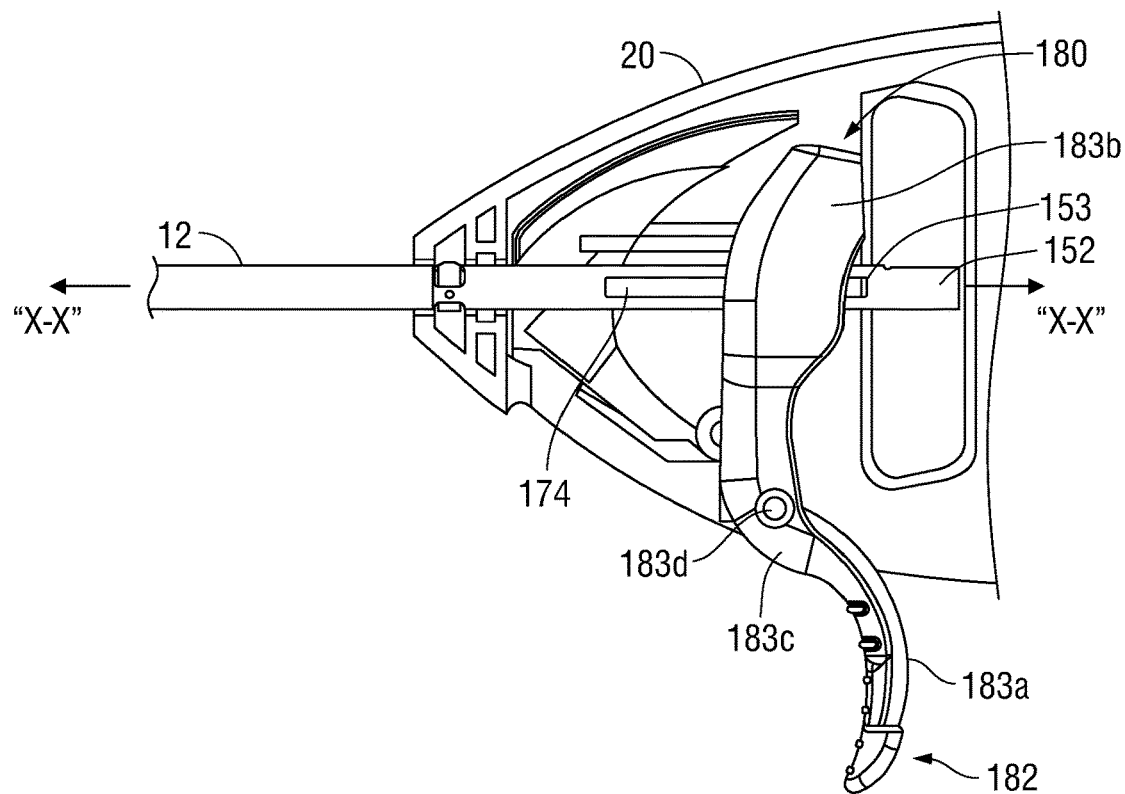
FIG. 5A is a side view of still another proximal portion of the electrosurgical forceps of FIG. 1 with portions removed to illustrate another trigger assembly thereof with the trigger disposed in the un-actuated position.
Figure 5B:
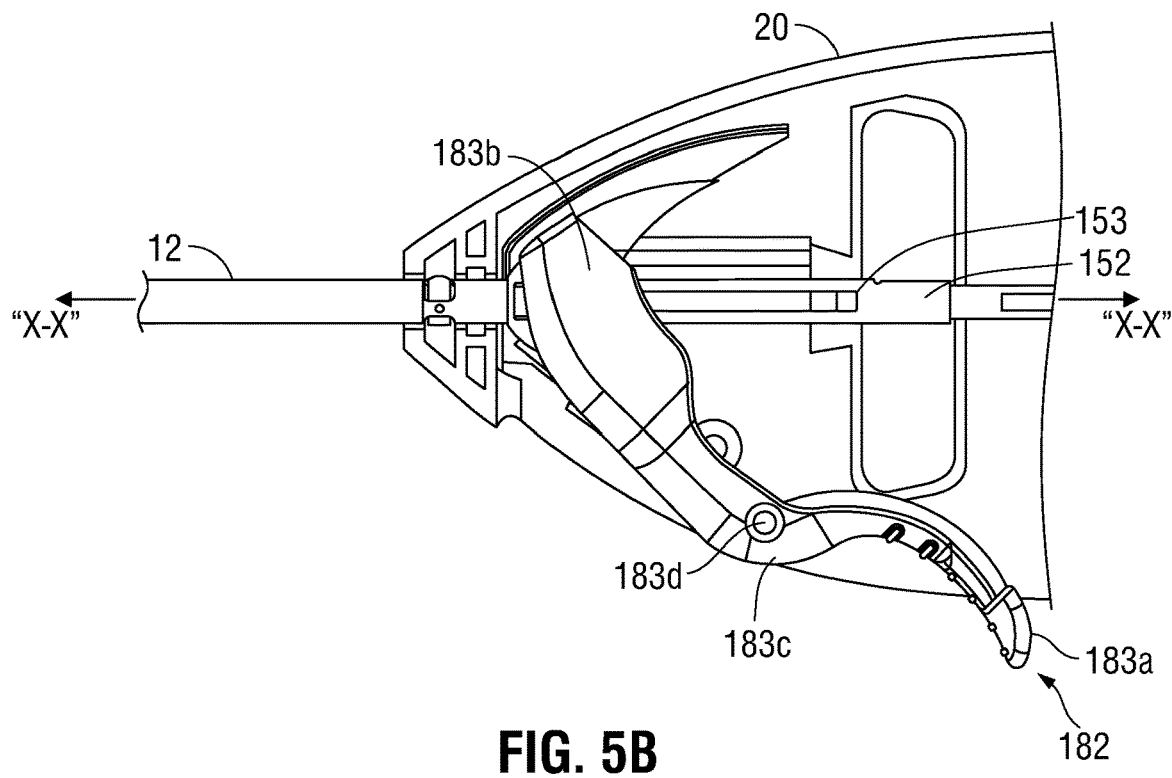
FIG. 5B is a side view of the proximal portion of the electrosurgical forceps shown in FIG. 5A with portions removed to illustrate the trigger assembly with the trigger disposed in the actuated position.
Figure 5C:
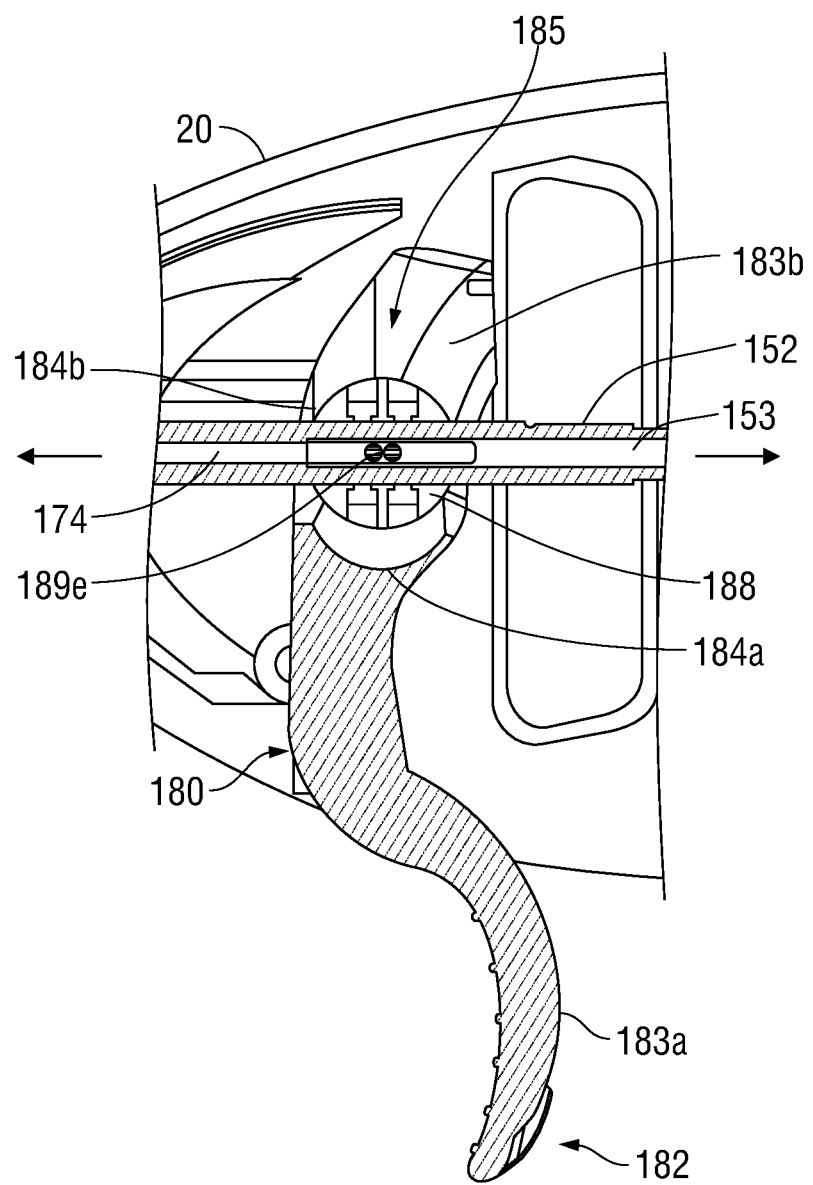
FIG. 5C is an enlarged, side, partial cross-sectional view of the proximal portion of the electrosurgical forceps shown in FIG. 5A with portions removed to illustrate the trigger assembly with the trigger disposed in the actuated position.
Figure 6A:
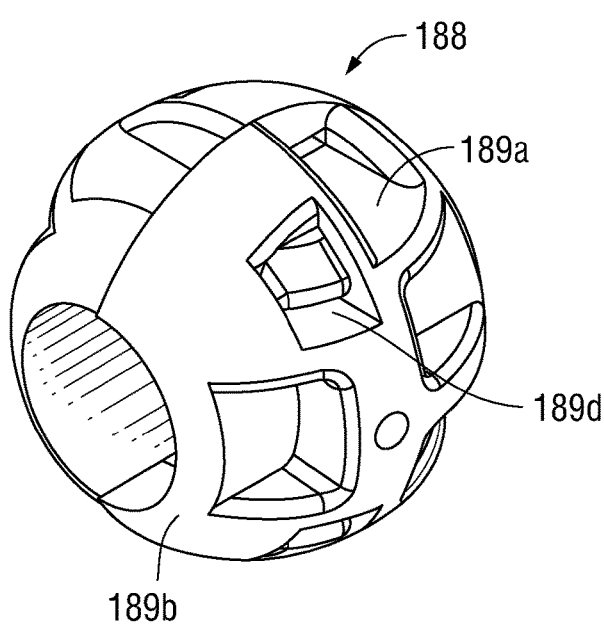
FIG. 6A is a perspective view the coupling sphere of the trigger assembly of FIG. 5A.
Figure 6B:
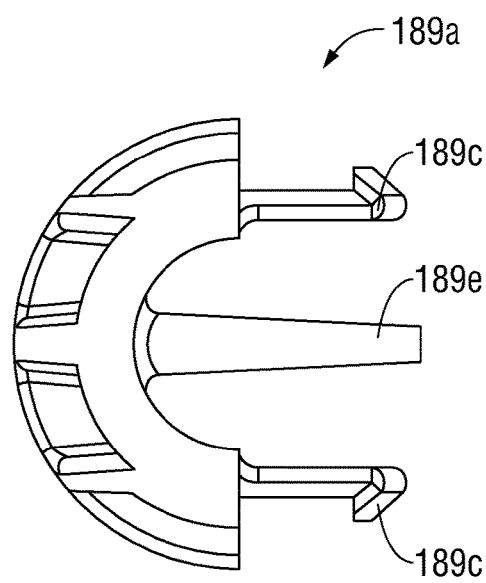
FIGS. 6B-6D are side, front, and top views, respectively, of one component of the coupling sphere of FIG. 6A.
Figure 6C:
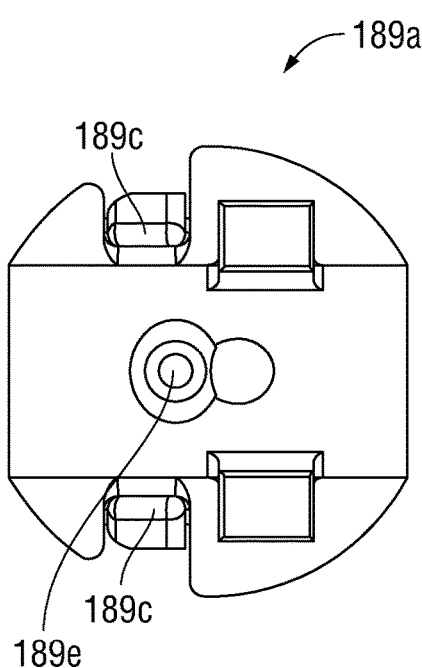
Figure 6D:
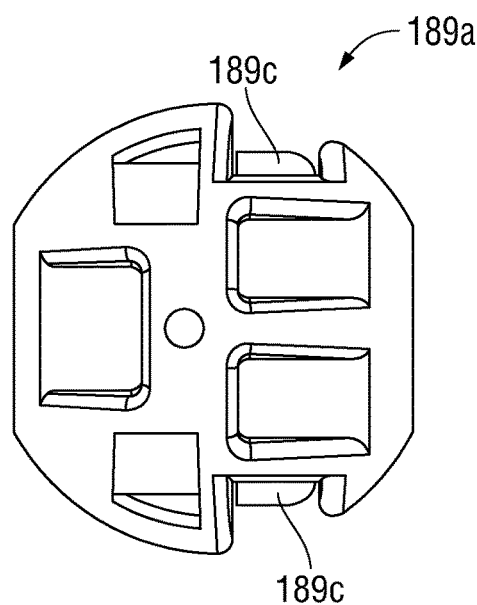
Figure 7C:
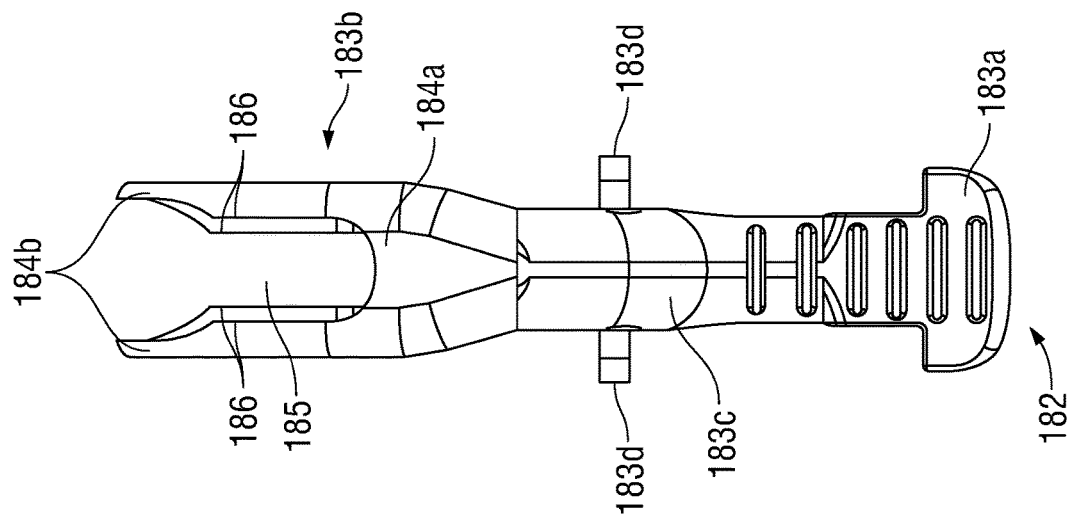
FIGS. 7A-7C are side, cross-sectional, and front views, respectively, of the trigger of the trigger assembly of FIG. 5A.
Figure 7B:
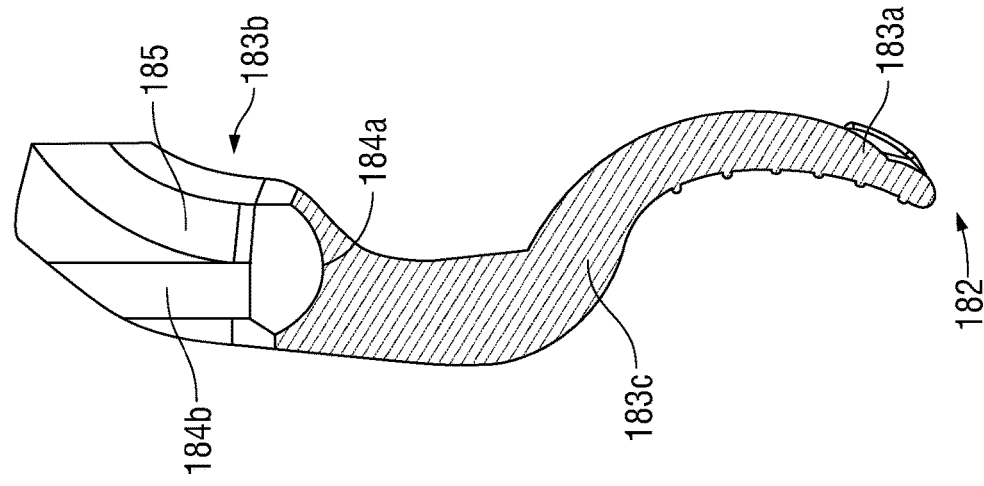
Figure 7A:
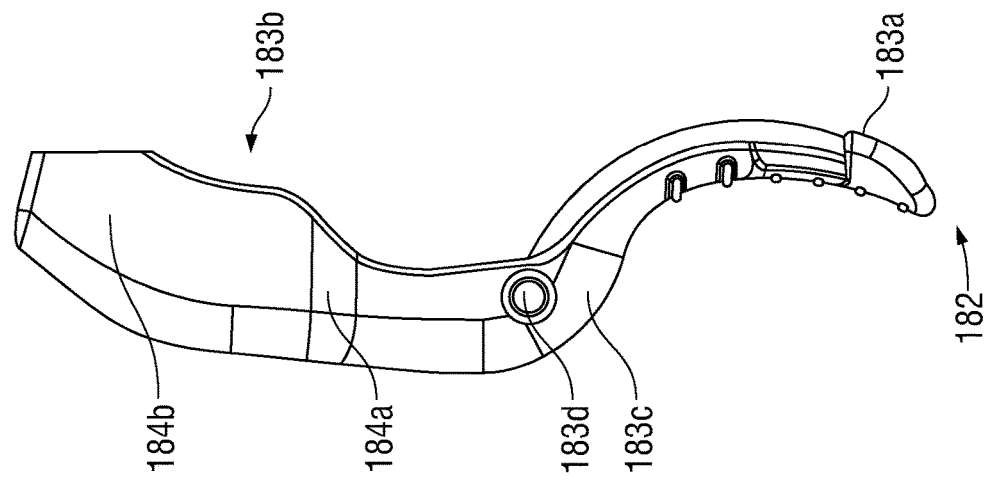

With reference to FIGS. 6A-6D, in conjunction with FIG. 5C, coupling sphere 188, as noted above, is rotatably captured within cavity 185 of retention portion 183 of trigger 182 (see FIG. 5C). Coupling sphere 188 is slidably disposed about drive bar 152 (e.g., defines a lumen extending longitudinally therethrough for receipt of drive bar 152) and is formed from first and second components 189a, 189b, e.g., hemispheres, engaged to one another, e.g., via snap-fit engagement of legs 189c within slots 189d. One of the first or second components 189a, 189b includes an internal post 189e or other suitable engagement structure(s) extending through longitudinal slot 153 defined within drive bar 152 and into engagement with knife bar 174 to fix coupling sphere 188 relative to knife bar 174. Coupling sphere 188 is slidable about drive bar 152 and along longitudinal axis "X-X" to thereby translate knife bar 174 to, in turn, deploy knife blade 172 distally through jaw members 110, 120 to cut tissue grasped between electrically-conductive surfaces 116, 126 and to retract knife blade 172 subsequent to tissue cutting (see FIG. 2A).

Returning to FIGS. 5A-7C, as a result of the above-detailed configuration, moving manipulation portion 183a of trigger 182 proximally relative to housing 20, e.g., from the un-acutated position (FIG. 5A) towards the actuated position (FIG. 5B), rotates pivot portion 183c counterclockwise (from the orientation illustrated in FIGS. 5A and 5B) relative to housing 20 to thereby move retention portion 183b distally. This distal movement of retention portion 183b, having coupling sphere 188 rotatably captured therein, urges coupling sphere 188 distally along longitudinal axis "X-X" (while allowing for rotation of retention portion 183b without imparting the same to coupling sphere). This distal translation of coupling sphere 188 translates knife bar 174 distally through shaft 12 and relative to end effector assembly 100 to deploy knife blade 172 distally through jaw members 110, 120 to cut tissue grasped between electrically-conductive surfaces 116, 126 (see FIG. 2A).

In embodiments, a return spring (not shown) may be provided to return manipulation portion 183a of trigger 182 towards the un-actuated position and, thus, to return knife blade 172 to the retracted position (FIG. 2A). Upon release of manipulation portion 183a of trigger 182 (in embodiments where a return spring is provided) or return of manipulation portion 183a of trigger 182 towards the un-actuated position, trigger 182 is pivoted clockwise (from the orientation illustrated in FIGS. 5A and 5B) relative to housing 20 to rotate pivot portion 183c clockwise (from the orientation illustrated in FIGS. 5A and 5B) relative to housing 20 to thereby move retention portion 183b proximally. This proximal movement of retention portion 183b pulls coupling sphere 188 proximally along longitudinal axis "X-X" about drive bar 152 and relative to housing 20 and shaft 12, thereby retracting knife blade 172 proximally from jaw members 110, 120 (see FIG. 2A).

Figure 8A:
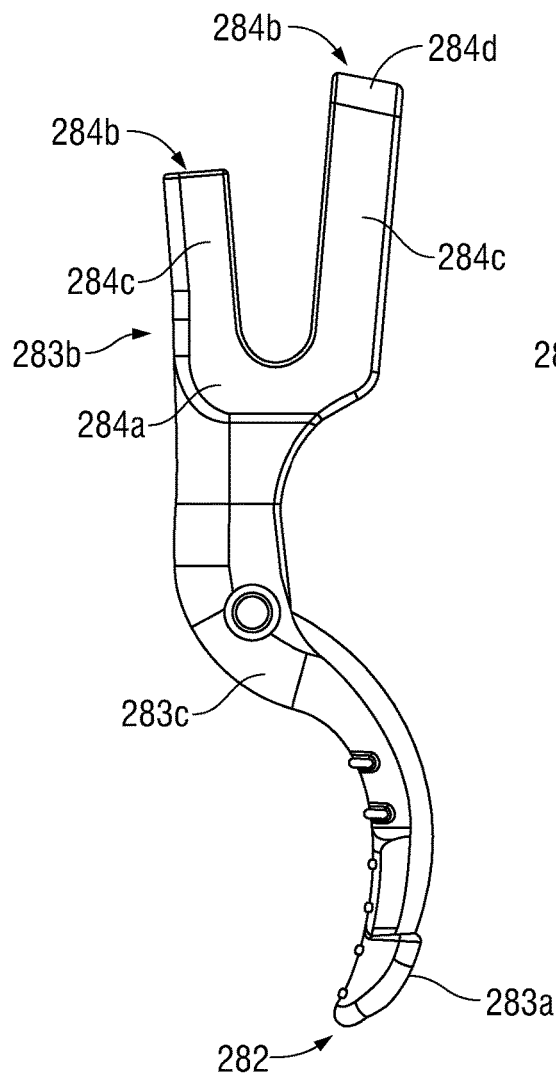
FIGS. 8A and 8B are side and perspective views, respectively, of another trigger configured for user with the trigger assembly of FIG. 5A.
Figure 8B:
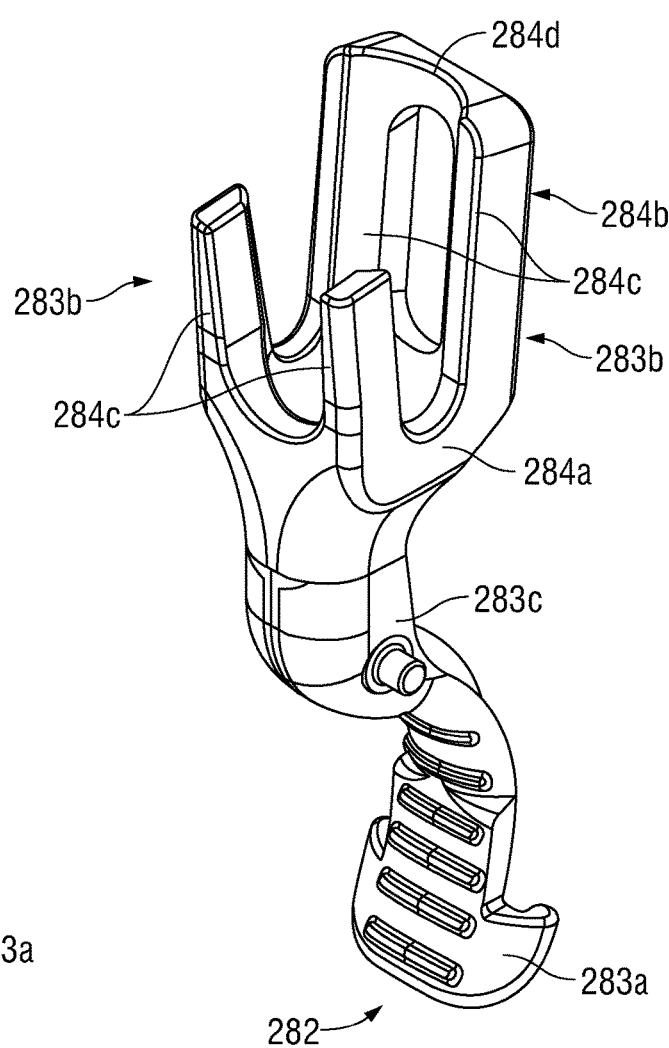

Turning to FIGS. 8A and 8B, another embodiment of a trigger 282 configured for use with trigger mechanism 180 (FIGS. 5A-5C) is shown. Trigger 282 is similar to trigger 182 (FIGS. 7A-7C) and, thus, only differences therebetween are described in detail below while similarities are summarily described or omitted entirely.

Trigger 282 includes a manipulation portion 283a, a retention portion 283b, and a pivot portion 283c. Retention portion 283b of trigger 282 defines a base 284a and pair of spaced-apart end forks 284b. Each end fork 284b includes first and second spaced-apart fork legs 284c configured for positioning on either side of drive bar 152 (see FIGS. 5A-5C). The spaced-apart fork legs 284c of the distal end fork 284b may be connected at free ends thereof via a connector 284d to increase structural support and rigidity, as it is the distal end fork 284b that is urged into contact with coupling sphere 188 (FIG. 5C) to deploy the knife blade 172 (FIG. 2A).

Base 284a and end forks 284b cooperate to define a cavity 285 configured to capture coupling sphere 188 (FIG. 5C) therein. Cavity 285 is at least partially defined by arcuate interior surfaces of base 284a and/or end forms 284b such that cavity 285 is at least partially complementary to coupling sphere 188 (FIG. 5C) about a proximal portion of coupling sphere 188 (FIG. 5C) to thereby provided smooth and consistent urging against a proximal portion of coupling sphere 188 (FIG. 5C) to translate coupling sphere 188 (FIG. 5C) distally as retention portion 283b is moved distally and rotated about pivot portion 283c.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
  a housing
  a shaft extending from the housing and defining a longitudinal axis;
  a drive bar extending from the housing at least partially through the shaft, the drive bar slidable relative to the housing and the shaft; and
  a trigger assembly, including:
    a trigger pivotably coupled to the housing on a first side of the longitudinal axis;
    a first linkage pivotably coupled to the housing on the first side of the longitudinal axis; and
    a second linkage pivotably coupled to both the trigger and the first linkage on a second side of the longitudinal axis opposite the first side of the longitudinal axis, the second linkage operably coupled to the drive bar such that pivoting of the trigger relative to the housing pivots the first linkage and moves the second linkage to slide the drive bar relative to the housing and the shaft, wherein the second linkage defines a T-shaped configuration including a crossbar and an upright, the trigger and first linkage pivotably coupled to the second linkage at opposing end portions of the crossbar, the second linkage operably coupled to the drive bar at a free end portion of the upright.

2. The surgical instrument according to claim 1, wherein the drive bar is slidable along the longitudinal axis.

3. The surgical instrument according to claim 2, wherein the second linkage is operably coupled to the drive bar along the longitudinal axis.

4. The surgical instrument according to claim 3, wherein the second linkage is operably coupled to the drive bar via a slider block slidable about the shaft within the housing and along the longitudinal axis.

5. The surgical instrument according to claim 1, further comprising a cutting element coupled to the drive bar such that sliding the drive bar relative to the housing and the shaft deploys the cutting element for cutting tissue.

6. The surgical instrument according to claim 1, wherein the trigger includes a manipulation portion that extends from the housing on the first side of the longitudinal axis to permit manual manipulation thereof by a user, and a linkage portion that extends within the housing across the longitudinal axis to the second side thereof, the second linkage pivotably coupled to the linkage portion of the trigger.

7. The surgical instrument according to claim 1, wherein the first linkage is pivotably coupled to the housing towards a first end of the first linkage on the first side of the longitudinal axis and extends within the housing across the longitudinal axis to a second end of the first linkage, the second linkage pivotably coupled to the first linkage towards the second end of the first linkage.

8. The surgical instrument according to claim 1, wherein at least a portion of at least one of: the trigger, the second linkage, or the first linkage defines a bifurcated configuration for receipt of the drive bar therebetween.

9. The surgical instrument according to claim 1, wherein at least one of: the trigger, the first linkage, or the second linkage is formed as a single, monolithic piece of material.

10. A surgical instrument, comprising:
a housing;
a shaft extending from the housing and defining a longitudinal axis;
a drive bar extending from the housing at least partially through the shaft, the drive bar slidable relative to the housing and the shaft; and
a trigger assembly, including:
a trigger pivotably coupled to the housing on a first side of the longitudinal axis and extending across the longitudinal axis to a second side of the longitudinal axis opposite the first side thereof;
a first linkage pivotably coupled to the housing on the first side of the longitudinal axis and extending across the longitudinal axis to the second side of the longitudinal axis;
a second linkage disposed on the second side of the longitudinal axis pivotably coupled to both the trigger and the first linkage on a second side of the longitudinal axis opposite the first side of the longitudinal axis, the second linkage operably coupled to the drive bar such that pivoting of the trigger relative to the housing pivots the first linkage and moves the second linkage to slide the drive bar relative to the housing and the shaft, wherein the second linkage defines a T-shaped configuration including a crossbar and an upright, the trigger and first linkage pivotably coupled to the second linkage at opposing end portions of the crossbar, the second linkage operably coupled to the drive bar at a free end portion of the upright.

11. The surgical instrument according to claim 10, wherein the drive bar is slidable along the longitudinal axis.

12. The surgical instrument according to claim 11, wherein the second linkage is operably coupled to the drive bar along the longitudinal axis.

13. The surgical instrument according to claim 12, wherein the second linkage is operably coupled to the drive bar via a slider block slidable about the shaft within the housing and along the longitudinal axis.

14. The surgical instrument according to claim 10, further comprising a cutting element coupled to the drive bar such that sliding the drive bar relative to the housing and the shaft deploys the cutting element for cutting tissue.

15. The surgical instrument according to claim 10, wherein the trigger includes a manipulation portion that extends from the housing on the first side of the longitudinal axis to permit manual manipulation thereof by a user.

16. The surgical instrument according to claim 10, wherein at least a portion of at least one of: the trigger, the second linkage, or the first linkage defines a bifurcated configuration for receipt of the drive bar therebetween.

17. The surgical instrument according to claim 10, wherein at least one of: the trigger, the first linkage, or the second linkage is formed as a single, monolithic piece of material.

18. The surgical instrument according to claim 10, further comprising an arcuate body operably coupled at one end to a distal end of the second linkage and pivotably coupled at an opposite end to the housing.

19. The surgical instrument according to claim 10, wherein the second linkage is operably coupled to the drive bar via a slider block slidable about the shaft and wherein the upright of the second linkage includes a slot defined in the upright configured to receive a pivot post configured to outwardly extend from the slider block.

20. The surgical instrument according to claim 19, wherein the slot is cam-shaped to vary the mechanical advantage of the slider block through the range of travel of the trigger.

* * * * *